US009427429B2

(12) United States Patent
Gray (10) Patent No.: US 9,427,429 B2
(45) Date of Patent: Aug. 30, 2016

(54) CANCER DIAGNOSIS AND IMAGING (75) Inventor: Lloyd S. Gray, Louisa, VA (US)

(73) Assignee: Tau Therapeutics LLC, Charlottesville, VA (US)

( * ) Notice: Subject to any disclaimer, the term of this patent is extended or adjusted under 35 U.S.C. 154(b) by 0 days.

(21) Appl. No.: 13/581,390

(22) PCT Filed: Feb. 28, 2011

(86) PCT No.: PCT/US2011/026416
§ 371 (c)(1),
(2), (4) Date: Aug. 27, 2012

(87) PCT Pub. No.: WO2011/109262
PCT Pub. Date: Sep. 9, 2011

(65) Prior Publication Data
US 2012/0321561 A1 Dec. 20, 2012

Related U.S. Application Data (60) Provisional application No. 61/309,030, filed on Mar. 1, 2010.

(51) Int. Cl.
A61K 31/4184 (2006.01)
A61K 31/675 (2006.01)
A61K 31/4015 (2006.01)
A61K 51/04 (2006.01)
A61K 33/24 (2006.01)
A61K 45/06 (2006.01)

(52) U.S. Cl.
CPC ....... A61K 31/4184 (2013.01); A61K 31/4015 (2013.01); A61K 31/675 (2013.01); A61K 33/24 (2013.01); A61K 45/06 (2013.01); A61K 51/0491 (2013.01)

(58) Field of Classification Search
None
See application file for complete search history.

(56) References Cited

U.S. PATENT DOCUMENTS

| 3,666,811 | A | 5/1972 | van der Stelt |
| 3,732,247 | A | 5/1973 | Helsley et al. |
| 4,535,073 | A | 8/1985 | Kimura et al. |
| 4,885,284 | A | 12/1989 | Seto et al. |
| 4,906,646 | A | 3/1990 | Honn et al. |
| 4,908,365 | A | 3/1990 | Buzas et al. |
| 4,957,927 | A | 9/1990 | Ferrand et al. |
| 5,171,752 | A | 12/1992 | Caldirola et al. |
| 5,508,403 | A | 4/1996 | Akiyama |
| 5,919,816 | A | 7/1999 | Hausheer et al. |
| 6,114,598 | A | 9/2000 | Kucherlapati et al. |
| 6,150,584 | A | 11/2000 | Kucherlapati et al. |
| 6,162,963 | A | 12/2000 | Kucherlapati et al. |
| 6,191,156 | B1 | 2/2001 | Kifor et al. |
| 6,251,886 | B1 | 6/2001 | Friedman |
| 6,255,457 | B1 | 7/2001 | Schnitzer |
| 6,372,719 | B1 | 4/2002 | Cunningham |
| 6,413,967 | B1 | 7/2002 | Gray et al. |
| 6,451,991 | B1 | 9/2002 | Martin et al. |
| 6,946,475 | B1 | 9/2005 | Gray et al. |
| 7,319,098 | B2 | 1/2008 | Cho et al. |
| 2002/0042405 | A1 | 4/2002 | Schuh |
| 2002/0165199 | A1 | 11/2002 | Klecker et al. |
| 2003/0144298 | A1 | 7/2003 | Curwen et al. |
| 2003/0158143 | A1 | 8/2003 | Gleave et al. |
| 2003/0207940 | A1 | 11/2003 | Shan et al. |
| 2005/0261202 | A1 | 11/2005 | Brown et al. |
| 2006/0003020 | A1 | 1/2006 | Petty et al. |
| 2006/0024365 | A1 | 2/2006 | Vaya et al. |
| 2006/0057063 | A1 | 3/2006 | Lappin et al. |
| 2006/0110332 | A1 | 5/2006 | Lewin et al. |
| 2007/0027194 | A1 | 2/2007 | Easterling et al. |
| 2007/0259867 | A1 | 11/2007 | Cho et al. |
| 2008/0139517 | A1 | 6/2008 | Reisberg |
| 2008/0194669 | A1 | 8/2008 | Gray et al. |
| 2009/0234019 | A1 | 9/2009 | Gray et al. |
| 2010/0087398 | A1 | 4/2010 | Krouse |
| 2010/0222406 | A1 | 9/2010 | Gray et al. |
| 2012/0088807 | A1 | 4/2012 | Krouse et al. |
| 2012/0264804 | A1 | 10/2012 | Gray et al. |
| 2013/0064814 | A1 | 3/2013 | Gray |

FOREIGN PATENT DOCUMENTS

| AU | 2011203315 | 7/2011 |
| CA | 2312195 | 6/1999 |
| CA | 2454643 | 2/2003 |
| CA | 2486622 | 12/2003 |
| CN | 101854802 | 10/2010 |

(Continued)

OTHER PUBLICATIONS

Molthoff et al. Monitoring response to radiotherapy in human squamous cell cancer bearing nude mice: comparison of 2'-deoxy-2'-[18F]fluoro-D-glucose (FDG) and 3'-[18F]fluoro-3'-deoxythymidine (FLT). 2007 Mol. Imaging Biol. 9: 340-347.*

Yang et al. Use of 3'-deoxy-3'-[18F]fluorothymidine PET to monitor early responses to radiation therapy in murine SCCVII tumors. 2006 Eur. J. Nucl. Med. Mol. Imaging 33: 412-419.*

Cohen et al. Thallium 201 myocardial imaging in patients with pulmonary hypertension. 1976 Circulation 54: 790-795.*

Wackers et al. Thallium-201 scintigraphy in unstable angina pectoris. 1978 Circulation 57: 738-742.*

Tonkinson et al. Cell cycle modulation by a multitargeted antifolate, LY231514, increases the cytotoxicity and antitumor activity of gemcitabine in HT29 colon carcinoma. 1999 Cancer Res. 59: 3671-3676.*

(Continued)

Primary Examiner — Michael G Hartley
Assistant Examiner — Jennifer Lamberski
(74) Attorney, Agent, or Firm — Fish & Richardson P.C.

(57) ABSTRACT

The present invention provides a method for imaging a disease or condition in a mammal which includes the steps of; administering a therapeutically effective amount of a cell cycle inhibitor to effectively stop proliferation of eukaryotic cells at a cell cycle checkpoint between the G1 and S phase, stopping administration of the cell cycle inhibitor for a period of time, administering a marker to the mammal and imaging the mammal.

21 Claims, 7 Drawing Sheets

(56) References Cited

FOREIGN PATENT DOCUMENTS

| | | |
|---|---|---|
| CN | 102112490 | 6/2011 |
| EP | 0353692 | 2/1990 |
| EP | 0805147 | 11/1997 |
| EP | 1609504 | 12/2005 |
| EP | 1698340 | 9/2006 |
| FR | 2 355 833 | 1/1978 |
| JP | 52156871 | 12/1977 |
| JP | 11246417 | 9/1999 |
| JP | 2009137378 | 6/2009 |
| WO | WO 92/05172 | 4/1992 |
| WO | WO 97/10212 | 3/1997 |
| WO | WO 99/29847 | 6/1999 |
| WO | WO 00/15845 | 3/2000 |
| WO | WO 00/59882 | 10/2000 |
| WO | WO 01/62740 | 8/2001 |
| WO | WO 02/069886 | 9/2002 |
| WO | WO 02/092127 A1 | 11/2002 |
| WO | WO 2004/000311 | 12/2003 |
| WO | WO 2005/077082 | 8/2005 |
| WO | WO 2005/079316 | 9/2005 |
| WO | WO 2005/086971 | 9/2005 |
| WO | WO 2006/003020 | 1/2006 |
| WO | WO 2006/023881 | 3/2006 |
| WO | WO 2006/023883 | 3/2006 |
| WO | WO 2008/018642 A2 | 2/2008 |
| WO | WO 2008/018642 A3 | 2/2008 |
| WO | WO 2008/077077 | 6/2008 |
| WO | WO 2008/141189 | 11/2008 |
| WO | WO 2009/137378 | 11/2009 |
| WO | WO 2010/141842 | 12/2010 |
| WO | WO 2011/109262 | 9/2011 |

OTHER PUBLICATIONS

Francis et al. In vivo imaging of cellular proliferation in colorectal cancer using positron emission tomography. 2003 Gut 52: 1602-1606.*

Heo et al. T-type Ca2+ channel blockers suppress the growth of human cancer cells. 2008 Bioorg. Med. Chem. Lett. 18: 3899-3901.*

Roderick et al. Ca2+ signalling checkpoints in cancer: remodelling Ca2+ for cancer cell proliferation and survival. 2008 Nat. Rev. Cancer 8: 361-375.*

Kubota et al. Active and passive mechanisms of [fluorine-18] fluorodeoxyglucose uptake by proliferating and prenecrotic cancer cells in vivo: a microautoradiographic study. 1994 J. Nucl. Med. 35: 1067-1075.*

Gray L.S. et al., "The Role of Voltage Gated T-Type $Ca^{2+}$ Channel Isoforms in Mediating "Capacitative" $Ca^{2+}$ Entry in Cancer Cells", *Cell Calcium* 36:489-497 (2004).

Asaga S. et al., "Identification of a New Breast Cancer-Related Gene by Restriction Landmark Genomic Scanning", *Anticancer Research* 26:35-42 (2006).

Al-Hajj et al., "Prospective identification of tumorigenic breast cancer cells," Proc. Natl. Acad. Sci. U.S.A., 100: 3983-3988, 2003.

Altschul et al., "Basic local alignment search tool," *J Molec. Biol.*, 1990, 215:403-410.

Bean and McDonough, "Two for T," Neuron, 1998, 20:825-828.

Benham et al., "Vanilloid and TRP channels: a family of lipid-gated cation channels," *Neuropharmacology*, 2002, 42:873-888.

Benzaquen, Laura R., et al. "Clotrimazole inhibits cell proliferation in vitro and in vivo", Nature Medicine, vol. 1, No. 6, Jun. 1995, pp. 534-540.

Berridge et al., "The versatility and universality of calcium signaling," *Nat. Rev. Mol Cell Biol.*, 2000, 1:11-21.

Bertolesi et al., The Ca2+ channel antagonists mibefradil and pimozide inhibit cell growth via different cytotoxic mechanisms, Mol. Pharmacol. 62:210-219,2002.

Bitko and Barik, "Phenotypic silencing of cytoplasmic genes using sequence-specific double-stranded short interfering RNA and its application in the reverse genetics of wild type negative-strand RNA viruses," BMC Microbiol., 1:34, 2001.

Brooks et al., "Over expression of the voltage-gated T-type calcium channel induces vascular smooth muscle cell proliferation," Circulation, 1999, 100(18):I-209, Abstract 1081.

Burton and Barbas, "Human Antibodies from combinatorial libraries," Adv Immunol., 1994, 57:191-280.

Buskens et al. (Digestive Disease Week Abstracts and Itinerary Planner, 2003, abstract No. 850).

Cahalan et al., "Molecular properties and physiological roles of ion channels in the immune system." *J Clin Immunol.*, 2001, 21:235-252.

Cao Z. et al., "Angiotensin Converting Enzyme Inhibition and Calcium Antagonism Attenuate Streptozotocin-Diabetes-Associated Mesenteric Vascular Hypertrophy Independently of Their Hypotensive Action", J Hypertension, 16(6):793-799 (1998).

Carrillo and Lipman, "The multiple sequence alignment problem in biology," *SIAM J Applied Math.*, 1988, 48: 1073-1082.

Carter et al., "Humanization of an anti-p185HER2 antibody for human cancer therapy," Proc. Natl. Acad. Sci. USA, 1992, 89:4285-4289.

Carter, S. K. et al. (Chemotherapy of Cancer; Second edition; John Wiley & Sons: New York, 1981; appendix C), 3 pages.

Cech, "Ribozymes and Their Medical Implications," JAMA, 260:3030-3034, 1988.

Chemin et al., "Specific contribution of human T-type calcium channel isotypes ($\alpha_{1G}$, $\alpha_{1H}$ and $\alpha_{1I}$) to neuronal excitability," *J Physiol (Lond)*, 2002, 540:3-14.

Clapham, "Sorting out MIC, TRP, and CRAC Ion Channels," *J Gen. Physiol.*, 2002, 120:217-220.

Clozel et al., "Voltage-gated T-type $Ca^{2+}$ channels and heart failure," *Proc Assoc. Am Physicians*, 1999, 111:429-437.

Cohen, R.B., et al. "Pilot study of pharmacologic inhibition of calcium entry blockers in the treatment of advanced breast and prostate cancer", Proc. Annu. Meet. Am. Soc. Clin. Oncol., vol. 16, 1997, p. 538a.

Colcher D. et al., "Use of Monoclonal Antibodies as Radiopharmaceuticals for the Localization of Human Carcinoma Xenografts in Athymic Mice", Methods in Enzymology, 121 :802-816 (1986).

Crunelli et al., "The 'window' T-type calcium current in brain dynamics of different behavioural states," J Physiol., 2005, 562:121-129.

Dalerba et al., "Cancer Stem Cells: Models and Concepts," *Annu. Rev. Med.*, 2007, 58:267-284.

Densmore et al., "A voltage operable current is involved in activation-induced $Ca^{2+}$ entry in human lymphocytes whereas $I_{CRAC}$ has no apparent role," *Am J Physiol.*, 1996, 271:C1494-C1503.

Densmore et al., "A voltage-gated calcium channel is linked to the antigen receptor in Jurkat T lymphocytes," *FEBS Lett*, 1992, 312:161-164.

Devereux et al., "A comprehensive set of sequence analysis programs for the VAX," *Nucleic Acids Res.*, 1984, 12:387-386.

Dogrul, A., et al., "Reversal of experimental neuropathic pain by T-type calcium channel blockers", Pain, 105, No. 1-2; XP-002473993, (2003), 159-168.

Dontu et al., "Role of Notch signaling in cell-fate determination of human mammary stem/progenitor cells," *Breast Cancer Res.*, 2004, 6:R605-R615.

Elbashir et al., "Duplexes of 21-nucleotide RNAs mediate RNA interference in cultured mammalian cells," Nature, 411:494-498, 2001.

Falch, E., et al., "GABA uptake inhibitors containing mono- and diarylmethoxyalkyl Nsubstituents", Drug Des Deliv., 4(3), (May 1989),205-215.

Foon et al., "Immune response to the carcinoembryonic antigen in patients treated with an anti-idiotype antibody vaccine," J. Clin. Invest. 96:334-342 (1995).

Gackiere, Florian, et al. "A role for voltage gated T-type calcium channels in mediating "capacitative" calcium entry?", Cell Calcium, vol. 39, No. 4, (Apr. 1, 2006),357-366.

Gura, "Systems for Identifying New Drugs Are Often Faulty," Science, 1997, 278:1041-1042.

Harper et al., "Functional T-type calcium channel expression is necessary for Gl-S progression in vascular smooth muscle," Circulation, 2000, 102(18):II-48 Abstract 222.

Haseloff and Gerlach, "Simple RNA enzymes with new and highly specific endoribonuclease activities," Nature, 334:585, 1988.

(56) References Cited

OTHER PUBLICATIONS

Haverstick D.M. et al., "Three Intracellular Signals for Cytotoxic T Lymphocyte-Mediated Killing", The Journal of Immunology, 146(10):3306-3313 (1991).
Haverstick et al., "Calmodulin regulation of $Ca^{2+}$ entry in Jurkat T cells," Cell Calcium, 1998, 23:361-368.
Haverstick et al., "Increased intracellular $Ca^{2+}$ induces $Ca^{2+}$ influx in human T lymphocytes," Molecular Biol Cell, 1993, 4:173-184.
Haverstick, Inhibition of Human Prostate Cancer Proliferation in Vitro and in a Mouse Model by a Compound Synthesized to Block CA2+ Entry, Cancer Research, Feb. 15, 2000, 60, pp. 1002-1008.
Heady et al., "Molecular pharmacology of T-type Ca2+ channels," Jpn. J. Pharmacol., 2001, 85:339-350.
Herlyn et al., "Anti-idiotype cancer vaccines: past and future," Cancer Immunol. Immunother. 43:65-76 (1996).
Hockerman et al., "Molecular determinants of drug binding and action on L-type calcium channels," Annu. Rev. Pharmacol Toxicol., 1997,37:361-396.
Hoth and Penner, "Calcium release-activated calcium current in rat mast cells," J. Physiol., 1993, 465:359-386.
Hoth, and Penner, "Depletion of intracellular calcium stores activates a calcium current in mast cells," 1992, Natur, 355:353-356.
Huguenard, "Block of T-Type $Ca^{2+}$ Channels is an Important Action of Succinimide Antiabsence Drugs," Epilepsy Currents, 2002, 2(2):49-52.
Imagawa et al., "Inhibitory Effect of Efonidipine on Aldosterone Synthesis and Secretion in Human Adrenocarcinoma (H295R) Cells", J Cardiovascular Pharmacology (2006), 47(1):133-138.
Jakobovits, "The long-awaited magic bullets: therapeutic human monoclonal antibodies from transgenic mice," Exp. Opin. Invest. Drugs 7(4): 607-614 (1998).
Jefferies et al., "A Catalytic 13-mer Ribozyme," Nucleic Acids Res., 17:1371-1377, 1989.
Jones, Cancer therapy: Phenothiazines in an unexpected role, Tumori, 1985, 71:563-5691.
Kaiser, "First Pass at Cancer Genome Reveals Complex Landscape," Science, 2006, 313:1370.
Kanda et al., "Naftopidil, a selective alpha-1 adrenoceptor antagonist, inhibits growth of human prostate cancer cells by G1 cell cycle arrest," Int. J. Cancer, 2008, 122(2):444-451.
Kansal, V. K, et al., "Possible Antihypertensive Agents: Syntheses of N-Aralkyl-bsubstituted Phenylethylamines & N-Alkyl/acyl-6,7-dimethoxY-I-[,(a-phenyl-b-substituted phenyl) ethyl]-I, 2,3,4-tetrahydroisoquinolines", Indian Journal of Chemistry, vol. 20B, 1(1982), 885-890.
Kim and Cech, "Three-dimensional model of the active site of the self-splicing rRNA precursor of Tetrahymena," Proc. Natl. Acad. Sci. USA, 84:8788-8792, 1987.
Klimatcheva and Wonderlin, "An ATP-sensitive K(+) current that regulates progression through early G1 phase of the cell cycle in MCF-7 human breast cancer cells," J Membr. Biol., 1999, 171(1):35-46.
Kohler G. et al., "Continuous Cultures of Fused Cells Secreting Antibody of Predefined Specificity", Nature, 256:495-497 (1975).
Krontiris and Capizzi (Internal Medicine, 4th Edition, Editor-in-chief Jay Stein, Elsevier Science, 1994 Chapters 71-72, pp. 699-729).
Lee et al., "Nickel block of three cloned T-type Ca channels: low concentrations selectively block αlH," Biophys J., 1999, 77:3042.
Lee, D., et al., "Randomized comparison of T-type versus L-type calcium-channel blockade on exercise duration in stable angina: Results of the Posicor Reduction of Ischemia During Exercise (PRIDE) trial", American Heart Journal, 144(1), (2002), 60-67.
Li et al., "Evidence that transgenes encoding components of the Wnt signaling pathway preferentially induce mammary cancers from progenitor cells," Proc. Natl. Acad. Sci. USA, 2003, 100:15853-15858.
Li et al., "Receptor-operated $Ca^{2+}$ influx channels in leukocytes: a therapeutic target?" Trends Pharmacol. Sci., 2002, 23:63-70.
Liu et al., "Mammary stem cells, self-renewal pathways, and carcinogenesis," Breast Cancer Res., 2005, 7:86-95.
Lory et al., "T-type calcium channels in differentiation and proliferation," Cell Calcium, 2006, 40:135-46.

Mallick et al., "MicroRNA reins in embryonic and cancer stem cells," RNA Biol., 2011, 8(3):415-426.
Mariot et al., "Overexpression of an $\alpha_{1H}$ (Cav3.2) T-type calcium channel during neuroendocrine differentiation of human prostate cancer cells," J Biol. Chem., 2002, 277:10824-10833.
Massie, B. M, et al., "Mibefradil: A Selective T-Type Calcium Antagonist", American Journal of Cardiology, 80(9, Supp 1), (1997), 231-321.
McCalmont et al., Design, Synthesis, and Biological Evaluation of Novel T-Type Calcium Channel Antagonists, Bioorganic & Medicinal Chemistry Letters, Jul. 16, 2004, 14, pp. 3691-3695.
McCalmont, W. F, et al., "Investigation into the structure-activity relationship of novel concentration dependent, dual action T-type calcium channel agonists/antagonists", Bioorg Med Chem., 13(11), (Jun. 1, 2005),3821-3839.
McDonald et al., "Regulation and modulation of calcium channels in cardiac, skeletal, and smooth muscle cells," Physiol Rev., 1994, 74:365-507.
Merrit and Rink, "Regulation of cytosolic free calcium in fura-2-loaded rat parotid acinar cells," J Biol. Chem., 1987 262:17362-17369.
Merritt et al., "Use of manganese to discriminate between calcium influx and mobilization from internal stores in stimulated human neutrophils," J Biol Chem., 1989, 264:1522-1527.
Mikaelian et al., "Proteotypic classification of spontaneous and transgenic mammary neoplasms," Breast Cancer Res., 2004, 6:R668-R679.
Monteil et al., "Molecular and f1H1ctional properties of the human $(\alpha_{1G})$ subunit that forms T-type calcium channels," J Biol. Chem., 2000, 275:6090-6100.
Mori et al., "Transient receptor potential 1 regulates capacitative $CA^{2+}$ entry and $CA^{2+}$ release from endoplasmic reticulum in B lymphocytes," J Exp. Med., 2002, 195:673-681.
Nebe B. et al., "Induction of Apoptosis by the Calcium Antagonist Mibefradil Correlates with Depolarization of the Membrane Potential and Decreased Integrin Expression in Human Lens Epithelial Cells", Graefe's Archive for Clinical and Experimental Ophthalmology 242(7):597-604 (2004), XP-002483831.
Neher and Sakmann, "The patch clamp technique," Scientific American March, 1992, 44-51.
Niwa, Noriko, et al , "Immunoblotting of T-type Ca2+ Channel Protein in Mouse Brain and Embryonic Heart by Using Two Antibodies against CAv3.1 Channels", Environmental Medicine, 47, (2003),42-44.
Orkin, "Embryonic stem cells and transgenic mice in the study of hematopoiesis," Int. J. Dev. Biol., 1998, 42:927-934.
Peng et al., "CaTl expression correlates with tumor grade in prostate cancer," Biochem. Biophys. Res. Commun., 2001, 282:729:734.
Putney Jr. and McKay, "Capacitative calcium entry channels," Bioessays, 1999, 21 :38-46.
Reubinoff et al., "Embryonic stem cell lines from human blastocysts: somatic differentiation in vitro," Nat Biotech., 2000, 18:399-404.
Reya et al., "Stem cells, cancer, and cancer stem cells," Nature, 2001, 414:105.
Riechmann et al., "Reshaping human antibodies for therapy," Nature, 1988, 332:323-327.
Rossler et al., "Aldosterone regulation of T-type calcium channels", The Journal of Steroid Biochemistry and Molecular Biology (Jun. 2003), vol. 85, Iss 2-5, pp. 383-388.
Shamblott et al., "Derivation of pluripotent stem cells from cultured human primordial germ cells," Proc. Natl. Acad. Sci. USA, 1998, 95:13726-31.
Shin, Jung-Bum, "Identification of genes involved in sensory neuron mechanotransduction", Dissertation zur Erlangung des Akademischen Grades Doktorum Rerum Naturalis, (Feb. 28, 2003), 1-109.
Sievers et al., "Selective Ablation of Acute Myeloid Leukemia Using Antibody-Targeted Chemotherapy: A Phase I Study of an Anti-CD33 Calicheamicin Immunoconjugate," Blood 93:11 3678-3684 (1999).
Sims et al., "A humanized CD18 antibody can block function without cell destruction," J Immunol., 1993, 151:2296.
Skryma et al., "Store depletion and store-operated $Ca^{2+}$ current in human prostate cancer LNCaP cells: involvement in apoptosis," J Physiol (Lond.), 2000, 527 Pt 1:71-83.

(56) References Cited

OTHER PUBLICATIONS

Slish et al., "Molecular biology of the calcium antagonist receptor," *Hypertension*, 1992, 19:19-24.
Song, K S, et al., "Expression of caveolin-3 in skeletal, cardiac, and smooth muscle cells", J Biol Chem. 271 (25), (Jun. 21, 1996), 15160-5.
Stella et al 'Prodrugs: Challenges and Rewards, Part 1' Biotechnology: Pharmaceutical Aspects, p. 24, 2007.
Taber's Cyclopedic Medical Dictionary (1985, F.A. Davis Company, Philadelphia, p. 274).
Talley, E. M., et al., "Low-voltage-activated calcium channel subunit expression in a genetic model of absence epilepsy in the rat", Molecular Brain Research, 75(1), (2000), 159-165.
Taylor et al., "Calcium signaling and T-type calcium channels in cancer cell cycling," World J Gastroenterol., 2008, 14:4984-4991.
Thomson et al., "ES cell lines derived from human blastocysts," *Sci.*, 1998, 282:1145-1147.
Thomson et al., "Isolation of a primate embryonic stem cell line," *Proc. Natl. Acad. Sci. USA*, 1995, 92:7844-8.
Tocris Bioscience. Efonidipine hydrochloride monoethanolate. Copyright 2011. Electronic Resource. Retrieved May 2, 2011. [http://www.tocris.com/dispprod.php?ItemId=241266].
Tsavaler et al., Trp-p8, a novel prostate-specific gene, is upregulated in prostate cancer and other malignancies and shares high homology with transient receptor potential calcium channel proteins. Cancer Res., 2001, 61:3760-3769.
Venkatachalam et al., "The cellular and molecular basis of store-operated calcium entry," *Nat. Cell Biol.*, 2002, 4:E263-E272.
Verhoeyen et al., "Reshaping human antibodies: Grafting an antilysozyme activity," Science, 1988, 239:1534-1536.
Wagner et al., "Immunological Responses to the Tumor-Associated Antigen CA 125 in Patients with Advanced Ovarian Cancer Induced by the Murine Monoclonal Anti-Idiotype Vaccine ACA 125," Hybridoma 16:33-40 (1997).
Wang et al., "Ca2+ influx via T-type channels modulates PDGF-induced replication of mouse fibroblasts," *Am. J. Physiol.*, 1993, 265(5 pt 1):C1239-C1246.
Weng et al., "Voltage-gated K+ channels are associated with cell proliferation and cell cycle of ovarian cancer cell," *Gynecol. Oncol.*, 2007, 104(2):455-460.
Wikstrom, Peter, et al. "Additional peptidyl diazomethyl ketones, including biotinyl derivatives, which affinity-label calpain and related cysteinyl proteinases", 1. Enzyme Inhibition, 1993, vol. 6, pp. 259-269.
Williams et al., "Myeloid leukaemia inhibitory factor maintains the developmental potential of embryonic stem cells," *Nature*, 1988, 336:684-7.
Yang et al., "Coexistence of High Levels of Apoptotic Signaling and Inhibitor of Apoptosis Proteins in Human Tumor Cells: Implication for Cancer Specific Therapy," *Cancer Res.*, 2003, 63:6815-6824.
Yoshida et al., "G1 cell cycle arrest by amlodipine, a dihydropyridine Ca2+ channel blocker, in human epidermoid carcinoma A431 cells," *Biochem Pharmacol.*, 2007, 73(7):943-953.
Yunker, A. M., et al., "Immunological Characterization of T-Type Voltage-Dependent Calcium Channel CAv3.1 (Alpha 1 G) and CAv3.3 (Alpha 1) Isoforms Reveal Differences in their Localization, Expression, and Neural Development", Neuroscience, 117, (2003), 321-335.
Zamore, "RNA interference: listening to the sound of silence," Nature Struc. Biol., 8:746-750, 2001.
Zhong et at., "A profile of alternative RNA splicing and transcript variation of CACNA1H, a human T-channel gene candidate for idiopathic generalized epilepsies," *Human Molecular Genetics*, 2006, 15(9):1497-1512.
International Application Serial No. PCT/US05/04281, International Search Report mailed Dec. 18, 2006, 2 pgs.
International Application Serial No. PCT/US05/04281, Written Opinion mailed Dec. 18, 2006, 3 pgs.
International Application Serial No. PCT/US05/29851, International Search Report mailed Jun. 4, 2008, 1 pg.
International Application Serial No. PCT/US05/29851, Written Opinion mailed Jun. 4, 2008, 3 pgs.
International Application Serial No. PCT/US2005/004281, International Preliminary Report on Patentability mailed Jan. 9, 2007, 4 pgs.
International Application Serial No. PCT/US2005/029851, International Preliminary Examination Report mailed Feb. 24, 2009, 4 pgs.
International Application Serial No. PCT/US2005/029862, International Search Report and Written Opinion mailed Jun. 8, 2006, 6 pgs.
International Application Serial No. PCT/US2005/029862, Written Opinion mailed Jun. 6, 2006, 5 pgs.
International Preliminary Report on Patentability in International Application No. PCT/US2010/037437, dated Dec. 6, 2011, 5 pages.
International Search Report and Written Opinion in International Application No. PCT/US2010/037437, dated Feb. 17, 2011, 8 pages.
International Search Report issued in PCT/US2012/054567, dated Dec. 6, 2012, 6 pages.
International Search Report and Written Opinion issued in PCT/US2011/026416, dated Sep. 23, 2011, 6 pages.
F.D. Hong et al., "Taxol, Vincristine or Nocodazole Induces Lethality in G1-Checkpoint-Defective Human Astrocytoma U373MG Cells by Triggering Hyperploid Progression", Carcinogenesis 20(7):1161-1168 (1999).
Orth J.D. et al., "Quantitative Live Imaging of Cancer and Normal Cells Treated With Kinesin-5 Inhibitors Indicates Significant Differences in Phenotypic Responses and Cell Fate", Mol Cancer Ther 7(11):3480-3489 (Nov. 2008).
Extended Supplementary European Search Report Jun. 18, 2013 from related Application No. 11751125.3.
Bendig, "Humanization of Rodent Monoclonal Antibodies by CDR Grafting," Methods: a companion to methods in enzymology, 1995, 8:83-93.
Casset et al., "A Peptide mimetic of an anti-CD4 monoclonal antibody by rational design," Biochem Biophysical Res Comm., 2003, 307:198-205.
MacCallum et al., "Antibody-antigen Interactions: Contact Analysis and Binding Site Topography," J Mol Biol., 1996, 262:732-745.
Mittman, S, et al., "*Homo sapiens* low-voltage-activated calcium channel alpha 13.2 subunit delta25B splice variant (CACNA 1 H) gene, exons 11 through 36, and partial cds; and tryptase gamma 1 (TPSG1) gene, exon 6 and partial cds.", Genbank, 2005, 8 pgs.
Paul, Fundamental Immunology, 3rd edition, 1993, pp. 292-295.
Skolnick and Fetrow, "From genes to protein structure and function: novel applications of computational approaches in the genomic era," TIBTECH, 2000, 18:34-39.
Vajdos et al., "Comprehensive Functional Maps of the Antigen-binding site of an Anti-ErbB2 Antibody Obtained with Shotgun Scanning Mutagenesis," J Mol Biol., 2002, 320:415-428.
Wu et al., "Humanization of a Murine Monoclonal Antibody by Simultaneous Optimization of Framework and CDR Residues," J Mol Biol., 1999, 294:151-162.
International Search Report (International Application No. PCT/US00/09310), Aug. 11, 2000, 4 pages.
International Preliminary Report on Patentability in International Application No. PCT/US2012/054567, issued Mar. 12, 2014, 4 pages.
Panner and Wurster, "T-type calcium channels and tumor proliferation," Cell Calcium. Aug. 2006;40(2):253-9.
Giorgio Santoni et al. "Functional role of T-type calcium channels in tumour growth and progression: prospective in cancer therapy," British Journal of Pharmacology, May 2012, 166(4):1244-1246.
Gray et al. "The pharmacology and regulation of T type calcium channels: New opportunities for unique therapeutics for cancer," Cell Calcium, Aug. 2006, 40(2):115-120 (abstract only).
Taylor J T et al. "Selective blockade of T-type Ca<2+> channels suppresses human breast cancer cell proliferation," Cancer Letters, Aug. 2008, 267(1):116-124 (abstract only).
Zhanping et al., "Voltage-gated K+ channels are associated with cell proliferation and cell cycle of ovarian cancer cell," Gyne Col Oncol, 2006, 104(2): 455-460.
Japanese Office Action in Japanese Application No. JP 2012-556123, dated Feb. 24, 2015, 12 pages (with English Translation).

* cited by examiner

CANCER DIAGNOSIS AND IMAGING

CROSS-REFERENCE TO RELATED APPLICATIONS

This application claims the benefit of U.S. Provisional Application No. 61/309,030 filed on Mar. 1, 2010.

BACKGROUND OF THE INVENTION

Conventional cancer imaging is inaccurate and imprecise. Typically a patient has a marker, or other chemical compound, injected into their circulatory system, waits about 1 hour and is then imaged using Positron Emission Tomography (PET). The 1 hour time frame is quite short and may not be representative of the general activity of the entire number of cancer cells.

The reason why conventional cancer imaging is inaccurate and imprecise is because, in part, the metabolic uptake of an imaging marker has a cell cycle-specific mechanism of action. More specifically, uptake of the imaging marker is a function of which part of the cycle targeted cell are in. During any given hour, which is the typical wait time between marker administration and imaging, the cancer cells to be imaged may be at any stage of the cell cycle and may uptake and absorb the marker at different rates and amounts. This variance, which exists between all of the cancer cells throughout the patient, can cause misleading results and improper diagnoses.

The cell cycle is the series of events occurring in a cell leading to its division and duplication. In eukaryotic cells, the cycle can be divided into two periods, interphase and mitosis. Transit through these two periods of the cell cycle is known as proliferation. During interphase, the cell grows, accumulates nutrients needed for mitosis and duplicates its DNA. During mitosis, the cell splits itself into two distinct daughter cells. Interphase includes three distinct phases, Gap 1 ($G_1$) phase, S phase and Gap 2 ($G_2$) phase while mitosis includes two processes. $G_1$ phase includes the cell increasing in size, biosynthetic activities of the cell increasing and the synthesis of enzymes needed for DNA replication in the subsequent step. S phase includes the beginning of DNA synthesis and replication of all of the chromosomes. $G_2$ phase lasts until the cell enters mitosis and includes protein synthesis including the production of microtubules for mitosis. Mitosis includes a process where the cell's chromosomes are divided between the two daughter cells and a cytokinesis process where the original cell's cytoplasm divides forming two distinct daughter cells. The cell cycle also includes a resting phase, typically referred to as $G_0$. The boundaries between the various phases, for example the boundary between the $G_1$ and S phase is referred to as a cell cycle checkpoint.

The progression of the cell cycle can be inhibited, so that a particular cell stops the cycle at a point, a cellular checkpoint, before proceeding to the next phase. Cell cycle checkpoints are located between the different phases of the cell cycle, with two of the checkpoints being at the interface between the $G_1$ and the S phase ($G_1$/S) and the interface between the $G_2$ and M phase. A cell cycle inhibitor can stop the progression of a cell from passing to the next phase, for example a cell can be inhibited at the $G_1$/S cell cycle checkpoint, which forces the cell to remain in the $G_1$ phase until the inhibitor is removed.

In any particular cancer cell population or tumor in an individual, the length of the cell cycle is variable. This variability is due to differing periods spent in $G_1$ of $G_0$ while the length of time from the beginning of S phase to the end of M phase is relatively constant.

Imaging using traditional markers relies on the increased uptake of the marker because of the increased metabolic activity of the cancer cells. This increased uptake is most noticeable once the cancer cells are in the S phase as opposed to the other cell cycle stages. If the majority of cancer cells to be imaged are not in the S phase during the typically one hour time span between administration and imaging, the image result may not be representative of the actual concentration and location of cancer cells.

What is desired is a treatment to arrest the cell cycle for a clinically relevant fraction of cells at the $G_1$/S cell cycle checkpoint, so that the efficacy of imaging markers can be enhanced.

SUMMARY OF THE INVENTION

The present invention provides a method for imaging a disease or condition in a mammal which includes the steps of: administering a therapeutically effective amount of a cell cycle inhibitor to effectively stop proliferation of eukaryotic cells at a cell cycle checkpoint between the $G_1$ and S phase, stopping administration of the cell cycle inhibitor for a period of time, administering a marker to the mammal and imaging the mammal.

DEFINITIONS

In describing and claiming the invention, the following terminology will be used in accordance with the definitions set forth below.

As used herein, the term "pharmaceutically acceptable carrier, vehicle or diluent" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

The term "therapeutically effective amount" means an amount of a compound of the present invention that ameliorates, attenuates, reduces or eliminates a particular disease or condition or prevents or delays the onset of a particular disease or condition.

By "mammal" it is meant to refer to all mammals, including, for example, primates such as humans and monkeys. Examples of other mammals included herein are rabbits, dogs, cats, cattle, goats, sheep, mice, rats and horses. Preferably, the mammal is a female or male human.

The expression "pre-cancerous condition" refers to a growth that is not malignant but is likely to become so if not treated. A "pre-cancerous condition" is also known as "pre-malignant condition" by one of ordinary skill in the art.

It is understood to one skilled in the art that "T type calcium channel blockers" are also known as "T type calcium channel inhibitors".

DETAILED DESCRIPTION OF THE INVENTION

The method for imaging a disease or condition in a mammal includes several steps. The method can be conducted for many reasons including diagnosis of a suspected disease or condition, screening for the impact of various treatments and the monitoring of the progress of treatment. Based on the images generated from the described method, a health care administrator can more easily determine a diagnosis, an impact of a treatment and the progress of a current treatment.

The method can be used to image various diseases or conditions, including unstable angina, hypertension, epilepsy, neuropathic pain, petit mal seizure, absence seizure, age related macular degeneration, cancer and pre-cancerous conditions. In other embodiments, the method can be used to image tumors and pre-cancerous tumors.

In the method for imaging a disease or condition, a cell cycle inhibitor is first administered in a therapeutically effective amount to stop proliferation of eukaryotic cells at the cell cycle checkpoint between the $G_1$ and S phase ($G_1/S$). Varying lengths of the cell cycle are determined predominately by the time spent in the $G_1$ phase. The lengths of the S, $G_2$ and M phases are relatively invariant. Because of this, any particular cell in a population will reside in $G_1$ for a period of time before the cell enters the S phase of the cell cycle. To stop the cell cycle from continuing past a cell cycle checkpoint, a cell cycle inhibitor can be administered.

The administration of a cell cycle inhibitor causes asynchronously proliferating cancer cells in a population to accumulate at $G_1/S$ as they proceed through the cell cycle because their ability to proceed to the S phase is arrested by the cell cycle inhibitor. For a cell to move from $G_1$ phase to S phase through the cell cycle checkpoint, the cell requires influx of extracellular calcium to trigger biochemical cascades that are necessary for the progression. Removal of calcium from the extracellular medium blocks cell cycle transit for each cell. Thus, each cell persists in $G_1$ phase as long as it would in the presence of extracellular calcium, but becomes locked in place when $G_1/S$ is reached without calcium, thereby synchronizing cells at $G_1/S$. Calcium influx to a cell is necessary for proliferation and transit through the cell cycle. This is further described in Example 1 below.

The administration of the cell cycle inhibitor increases the percentage of cells at $G_1/S$. To take advantage of the increase of cells at $G_1/S$, administration of cell cycle inhibitor to the mammal persists for a period of time before imaging. This period of time can be between about 1 day and about 10 days, inclusively. In another embodiment, this period of time can be between about 5 days and about 7 days, inclusively. Although the upper limits of these embodiments are 10 days and 7 days, the cell cycle inhibitor can be administered for longer periods of time. The dosage of cell cycle inhibitor creates a concentration in a mammal's plasma of about 1 µM to about 10 µM.

The cell cycle inhibitor can be administered through several routes including parenteral, intravenous, intramuscular, intraperitoneal, intrathecal, suppository, transdermal, topical, or oral. Oral administration of the cell cycle inhibitor is most preferred. An oral administration can be administered as a dosage unit, typically a pill or capsule along with a pharmaceutically acceptable carrier.

The cell cycle inhibitor can be one or many of several cell cycle inhibitors. For example, mibefradil, efonidipine, ethosuximide, TTL-1177 (a proprietary compound, described in reference: Gray, L. S., Perez-Reyes, E., Gomora, J. C., Haverstick, D. M., Shattock, M., McLatchie, L., Harper, J., Brooks, G., Heady, T., and MacDonald, T. L. (2004) *Cell Calcium* 36, 489-497) and nickel.

These cell cycle inhibitors inhibit the influx of extracellular calcium into the cell which is critical for a number of vital cellular processes. The calcium necessary for these processes comes from the extracellular milieu via influx through calcium channels. Calcium channels are grouped into several families based upon sequence analysis, biophysical characteristics and pharmacological sensitivity. Among these is the T type calcium channel family. These calcium channels have been implicated in regulation of blood pressure, cardiac rhythm and cellular proliferation. Studies also suggest that T-type calcium channels may play an important role in age related macular degeneration. At least one pharmacological agent, mibefradil, has been proven to be clinically effective because of inhibition of T channel function. Inhibitors of calcium entry are useful for treating hypertension, cardiac arrhythmia and clinically deleterious cellular proliferation.

T type calcium channels are present in cells, cell lines and specifically cancer cell lines. Specifically, the Cav3.2 isoform of T type calcium channels has been shown to be aberrantly expressed in breast cancer tissue as compared to normal adjacent breast tissue in Japanese women, as discussed in reference Asaga, S., Ueda, M., Jinno, H., Kikuchi, K., Itano, O., Ikeda, T., and Kitajima, M. (2006) *Anticancer Res* 26, 35-42.

Cell cycle inhibitors effectively stop proliferation of eukaryotic cells at cell cycle checkpoints, including $G_1/S$, which is further explained in Examples 2-4 below.

Subsequent to the administration of the cell cycle inhibitor, an imaging marker is administered that is targeted to be uptaken in the S phase of the cell cycle. The period between the first administration of the cell cycle inhibitor and the imaging marker allows the accumulation of cells at $G_1/S$ of the cell cycle. This method increases the percentage of the cells which are in the S phase, thereby increasing the uptake of imaging marker into those cells.

Subsequent to administration of the cell cycle inhibitor, there is a period during which no cell cycle inhibitor is added. This period can range from about 30 minutes to about 72 hours. This period allows the cells which have accumulated at $G_1/S$ to enter the S phase of the cell cycle. About 5% to about 25% of cells will have accumulated at $G_1/S$. The increase in number of cells in the S phase makes a subsequent administered dose of an imaging marker more effective because a large percentage of cells will uptake the imaging marker in each dose.

Subsequent to the period where no cell cycle inhibitor is added, an imaging marker is administered to be uptaken or absorbed by cells in the S phase. The specific imaging marker will be dictated by clinical experience of one skilled in the art, where different diseases are imaged with different imaging markers. The same dose of an imaging marker is uptaken more readily and more specifically as compared to an imaging marker when used alone. The increase in imaging marker being uptaken is further described in Example 5 below.

Cancer cells can be located within the living body by administering a substance that binds to T type calcium channels or T type calcium channel accessory proteins. The location within the body of the drug can then be determined by tagging it with substances that are detectable from outside the body. For example, radioactive atoms can be localized within the body by measurements taken outside of it and examples of such atoms useful for this purpose include 99 mTc, 125I, 131I, 18F, 11C, 13N, 15O, 3H, 68Ga, 67Ga and 16F, among others. Some of the examples of the many possible imaging markers include $^{11}C$ Methionine, 2-deoxy-2-($^{18}F$)fluoro-D-glucose (FDG), tritiated FDG (3H-FDG) and fluoro deoxythymidines such as [18F]-3'-fluoro-3'-deoxy-L-thymidine). Additionally, deuterium, for example, can be similarly localized using Nuclear Magnetic Resonance (NMR) and various dyes, fluorescent as well as non-fluorescent, are localized using optical techniques. Additionally, one or more imaging markers may be combined and administered to the mammal prior to imaging of the mammal.

The administration of a cell cycle inhibitor followed by stopping that administration allows for a greater percentage of cells in a particular phase of the cycle. Various cellular metabolic activities proceed to differing extents in the various phases of the cell cycle. By altering the proportion of cancer cells in a particular phase of the cell cycle, an altered proportion will exhibit the metabolic activities most characteristic of that phase. One example of an imaging marker is FDG which is accumulated in cells that require this energy source for the particular metabolic state they are in. Thus imaging of FDG from outside the body would localize those cancer cells that responded to T type calcium channel active agents by an alteration in the fraction of cells in that part of the cell cycle most in need of glucose. Because, as an example, cancer cells preferentially express T type calcium channel function compared to non-cancerous cells, cancer cells will be preferentially affected by T type calcium targeting agents and detected.

After the imaging marker is administered to the mammal, the mammal is then imaged. The imaging marker can be administered at any suitable dose, for example about 100 mBq to about 600 mBq. The mammal can be imaged using any suitable imaging apparatus, for example an apparatus capable of gathering a magnetic resonance image (MRI), a positron emission tomogram (PET scan) or a computer tomogram (CT scan). The images gleaned by a suitable imaging apparatus will be more sensitive than images taken of mammals with no pre-treatment of a cell cycle inhibitor. The scans taken after administration of cell cycle inhibitors will be more sensitive because the diseased cells will have a higher uptake of the imaging markers as compared to uptake of imaging markers of cells that have not had an administration of a cell cycle inhibitor.

The above described method can be repeated as desired for each instance the mammal is to be imaged. For example, after the mammal received the administrations of cell cycle inhibitor, stopped administration of the cell cycle inhibitor, was administered an imaging marker and was imaged, the mammal can then again begin the process by receiving another administration of a cell cycle inhibitor. This method can be repeated as many times as desired, according to the requirements and advice of a qualified health care administrator.

The above described method is not only useful for imaging diseases and conditions such as cancer during treatment or diagnosis, the above described method could be used to aid in screening for which types of tumors are more and less affected by T-type calcium channel blockers and which types of tumors are more and less affected by a treatment. For instance, T-type calcium channel blockers are variably efficient at halting the cell cycle based on the type of tumor being targeted. For instance a pancreatic cancer tumor may react differently as compared to a pancreatic tumor in response to a dosage of T-type calcium channel blockers. Using the above described regimen for screening, it can be determined which types of tumors respond more efficiently to the regimen and what types of tumors do not respond as efficiently to the regimen. This information can be determined for each individual prior to undergoing a treatment regimen and can be used to plan the treatment regimen in the most efficient and advantageous way.

Example 1

Figure 1:
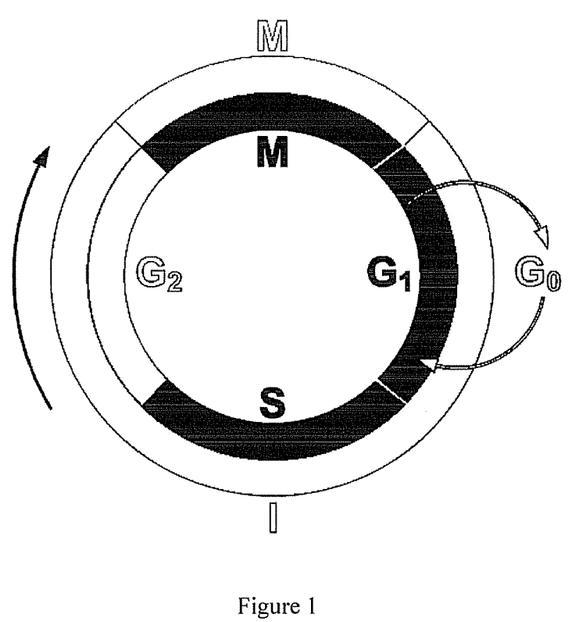
FIG. 1 is a schematic representation of the cell cycle. The outer ring includes the interphase (I) and mitosis (M) stages, with the duration of mitosis in relation to the other phases being exaggerated. The inner ring includes the Gap 1 ($G_1$), Gap 2 ($G_2$) and synthesis (S) phases. Gap 0 ($G_0$) or resting phase is not shown.
Figure 2:
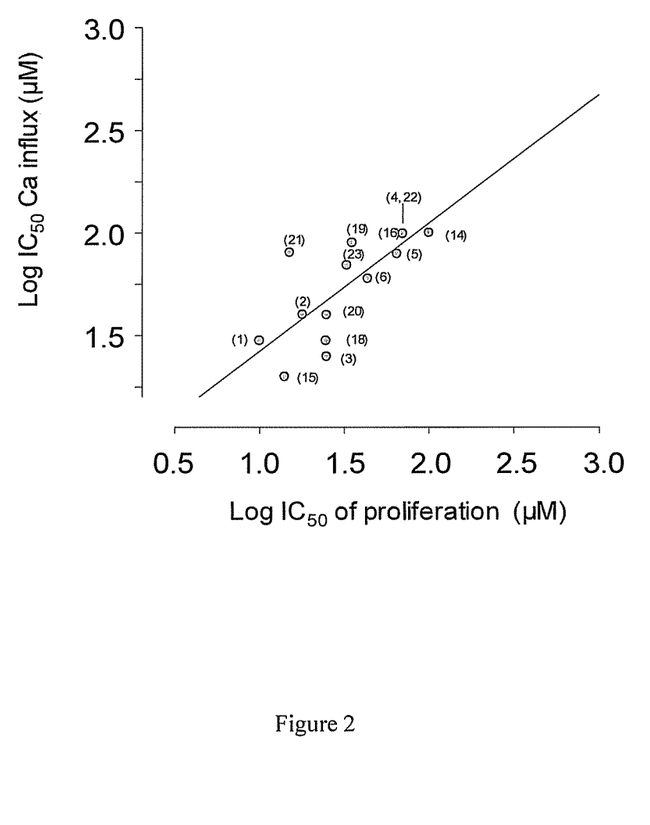
FIG. 2 is a graphical representation of the ability of several chemical agents to inhibit calcium influx as compared to the same chemical agent's ability to inhibit cell proliferation.

To measure the correspondence between calcium influx inhibition and proliferation, the ability of several chemical agents to inhibit calcium influx was plotted against the ability of the same agent to inhibit proliferation, as can be seen in FIG. 2 below. These agents were proprietary chemical entities synthesized at the University of Virginia. A least squares correlation line with a slope of 0.98 and $R^2$ value of 0.92 was obtained. Conventionally, a correlation cannot be used to infer causality, but in this case, a Bayesian approach is warranted because calcium influx is necessary a priori for proliferation, such that blocking calcium entry will correspondingly block proliferation. A regression line with a slope very near 1 means that essentially all of the variation in the variables is accounted for by variation in the other, meaning that there is no action of these agents on proliferation other than inhibition of calcium entry.

Example 2

Figure 3:
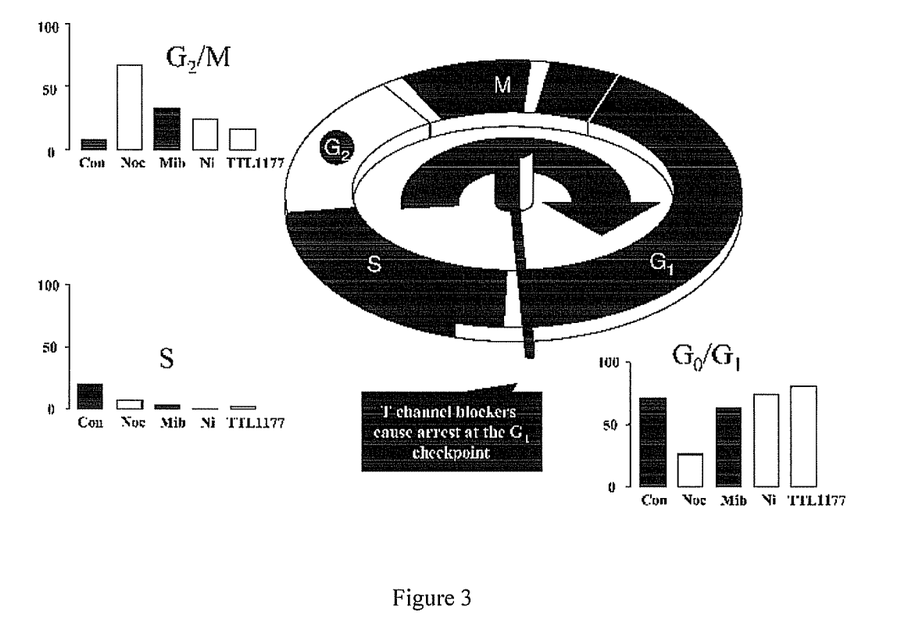
FIG. 3 is a schematic representation of the cell cycle and the influence several calcium channel blockers have on the progression of the cell cycle.

Cell cycle analysis was performed using flow cytometry and BUdR staining. In FIG. 3, "Con" represents untreated, control cells. All other cell cultures were treated with nocodazole, which interferes with microtubule polymerization and blocks the cell cycle during M phase. Treatment of A10 cells with nocodazole alone blocked cell cycle transit through M phase as determined by flow cytometry. Because A10 cells reside primarily in the cell cycle checkpoint between $G_0$ and $G_1$ (See "Con" in FIG. 3), evaluating the possibility that a pharmacologic agent inhibits transit out of that phase is not as straightforward as determining blockade at other cell cycle checkpoints. Therefore, cell cultures were treated for 24 hours with T channel calcium channel blockers mibefradil (mib), nickel (Ni) or TTL-1177 (a proprietary compound owned by the assignee Tau Therapeutics), before adding nocodazole. Absent an effect on the T channel blockers, cells would be locked at the cell cycle checkpoint between $G_2$ and M by nocodazole as happened with cells treated with it alone. Instead, treatment with the T type calcium channel blockers arrested cells at the cell cycle checkpoint between $G_0$ and $G_1$ and prevented accumulation at the cell cycle checkpoint between $G_2$ and M that would otherwise have resulted from nocodazole. This shows that T type calcium channel blockers arrest cycling cells at $G_1$/S.

Example 3

Figure 4:
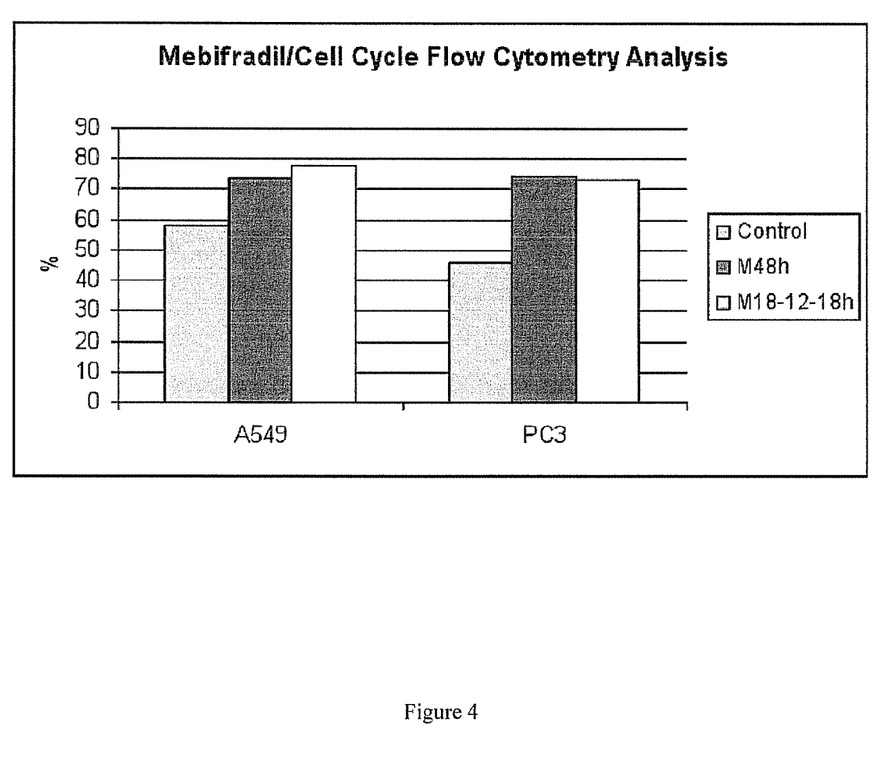
FIG. 4 is a graphical representation of data measuring the impact of mibefradil on cell cycles.

To measure the efficacy of the cell cycle inhibitor mibefradil at stopping progression through the cell cycle, human lung cancer cells of cell line A549 and human prostate cancer cells of cell line were incubated with 10 µM mibefradil for 48 hours (M48H). As can be seen in FIG. 4, the mibefradil increased the proportion of cells in the G1 phase of the cell cycle by not allowing progression to the S phase, for both cell lines. Further data was collected by incubating the same cell lines with 10 µM of mibefradil for 18 hours followed by a 12 hour washout followed by another 8 hour incubation with mibefradil (M18-12-18h). These results also show a greater proportion of cells in the G1 phase as compared to control cells not incubated with mibefradil.

Example 4

Figure 5:
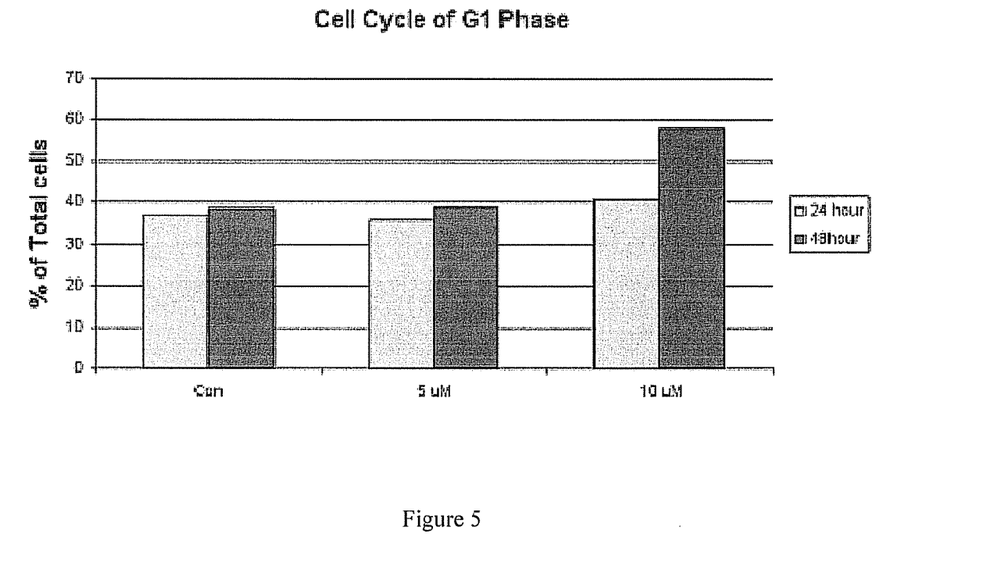
FIG. 5 is a graphical representation of data measuring the impact of mibefradil on cell cycles.

To measure the effect of mibefradil on the cell cycle of human prostate cancer cells of cell line PC3, PC3 cells were incubated with varying concentrations of mibefradil for varying times. The PC3 cells were incubated with either a 5 µM concentration or a 10 µM concentration for either 24 hours or 48 hours. As can be seen in FIG. 5, an increase in concentration and contact time of the mibefradil increases the proportion of cells in the G1 phase.

Example 5

The efficacy of the uptake of imaging markers after treatment with a cell cycle inhibitor was determined. Human colon cancer cells, cell line HT29, were first incubated for 24 hours with the cell cycle inhibitor mibefradil at concentrations of 5 µM (5 uM-FDG-HT29) and 10 µM (10 uM-FDG-HT29). After 24 hours of incubation with the mibefradil, the HT29 cells were removed from mibefradil contact. After 60 minutes of being removed from mibefradil contact, the imaging marker 2-deoxy-2-($^{18}$F)fluoro-D-glucose (hereinafter, "FDG") was administered.

Figure 6:
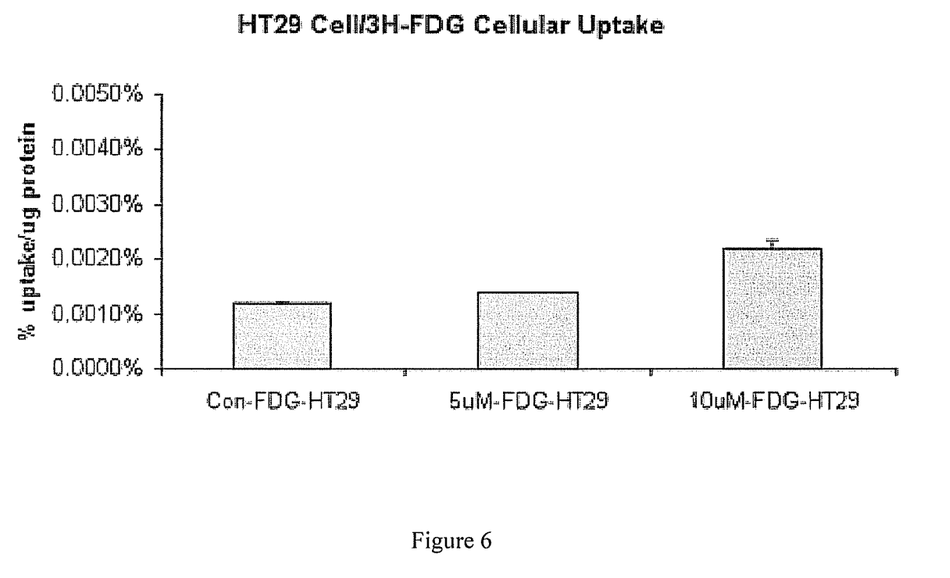
FIG. 6 is a graphical representation of data measuring uptake of an image marker after administration of mibefradil.

As can be seen in FIG. 6, uptake of the imaging marker FDG into the HT29 cells increased in the cells incubated with mibefradil as compared to the cells that were not incubated. With a concentration of 10 µM of mibefradil, the increase in uptake of FDG was about 100% as compared to uptake of cells not incubated with mibefradil.

Figure 7:
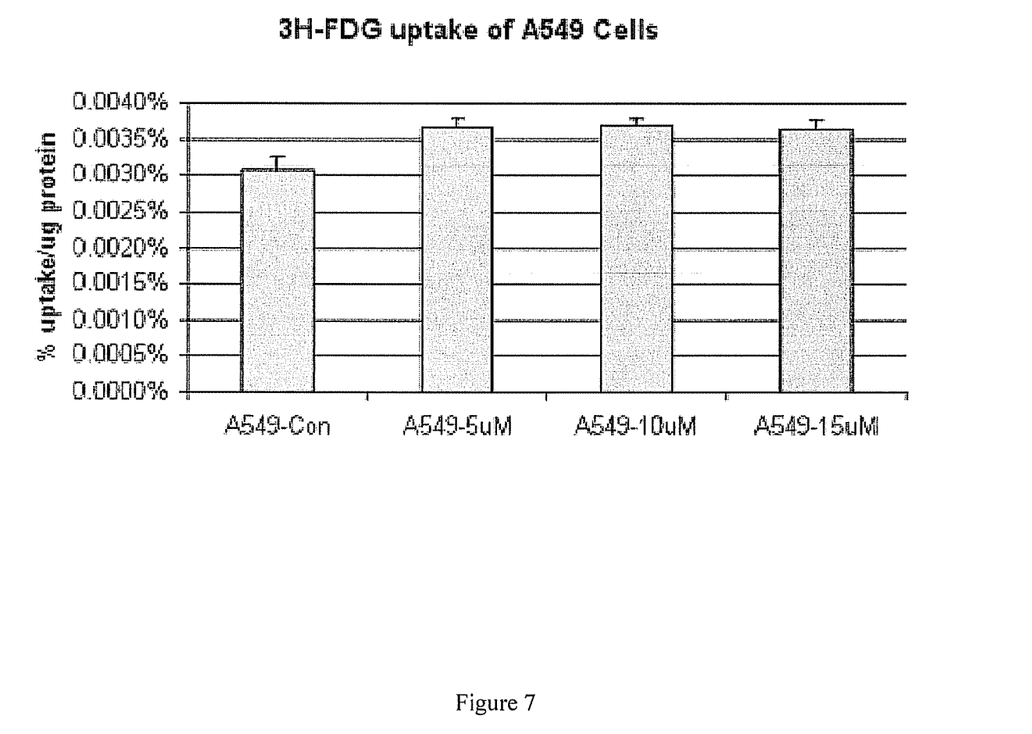
FIG. 7 is a graphical representation of data measuring uptake of an image marker after administration of mibefradil.

The uptake of an imaging marker was also determined in human lung cancer cells of cell line A549. A549 cells were incubated with 5 µM, 10 µM and 15 µM concentrations of the cell cycle inhibitor mibefradil for 24 hours. After 24 hours of incubation with the mibefradil, the A549 cells were removed from mibefradil contact. After 30 minutes of being removed from mibefradil contact, the imaging marker tritiated FDG (hereinafter "3H-FDG") was administered. As can be seen from FIG. 7, uptake of the 3H-FDG was maximal at 5 µM, with an increase in uptake being observed at all concentrations of mibefradil incubation. Although not shown, incubation of human prostate cancer cells of the PC3 cell line with 10 µM mibefradil for 72 hours increased uptake of the subsequently introduced imaging marker 3H-FDG by about 60%.

Example 6

As a descriptive example, the method for imaging a disease or condition in a mammal will be described as it would be undertaken in a clinical setting. Initially a mammal, in this embodiment the mammal is a human, is chosen to be imaged. This choice can be made based on various factors including past treatment for a disease, in this embodiment prostate cancer, or as a possible confirmation of a diagnosis. The human initially receives an administration of a cell cycle inhibitor in a therapeutically effective amount, in this embodiment an oral pill delivering a dosage of mibefradil twice daily for 6 days prior to a scheduled imaging session. After the 6 days of dosages are administered, the administration of mibefradil is ceased. After ceasing administration, there is a period of time before the imaging procedure is undertaken. In this example, 6 hours pass between ceasing administration of the mibefradil and administration of an imaging marker, which in this example is FDG. After 6 hours have passed, FDG is injected into the human at a sufficient dosage. The human is then imaged with a PET scan. The data produced from the PET scan is more precise and more accurate than data available from PET scans wherein the patient did not receive a cell cycle inhibitor.

What is claimed is:

1. A method for increasing the sensitivity of imaging a cancerous or pre-cancerous disease in a mammal which comprises the steps of:
    (a) administering to the mammal an effective amount of a T-type calcium channel inhibitor that inhibits proliferation of cancerous or pre-cancerous diseased cells by inhibiting cell cycle progression through the checkpoint between the G1 and S phase wherein the diseased cells accumulate at the G1/S checkpoint of the cell cycle;
    (b) subsequently administering an imaging marker to the mammal after a period wherein cells that have accumulated at the G1/S checkpoint of the cell cycle following administration of the T-type calcium channel inhibitor have progressed to the S phase of the cell cycle, resulting in an increased proportion of the diseased cells in the S phase of the cell cycle; and (c) imaging the mammal with an imager and obtaining an image of diseased cells with greater sensitivity compared with imaging in the absence of administration of the T-type calcium channel inhibitor.

2. The method of claim 1, wherein the disease is a cancerous or pre-cancerous tumor.

3. The method of claim 1, wherein the mammal is a human.

4. The method of claim 1, wherein the T-type calcium channel inhibitor is selected from the group consisting of mibefradil, efonidipine, ethosuximide, TTL-1177, and nickel and combinations thereof.

5. The method of claim 1, wherein the imaging marker is selected from the group consisting of $^{11}$C-methionine, 2-deoxy-2-($^{18}$F)fluoro-D-glucose, and [$^{18}$F]-3'-fluoro-3'-deoxy-L-thymidine and combinations thereof.

6. The method of claim 5, wherein the imaging marker is [$^{18}$F]-3'-fluoro-3'-deoxy-L-thymidine.

7. The method of claim 1, wherein the T-type calcium channel inhibitor is administered for between about 1 and about 10 days, inclusively, prior to administering the imaging marker.

8. The method of claim 7, wherein the T-type calcium channel inhibitor is administered for between about 5 and about 7 days, inclusively, prior to administering the imaging marker.

9. The method of claim 1, wherein the administration of the T-type calcium channel inhibitor is stopped for about 30 minutes to about 72 hours prior to administration of the imaging marker.

10. The method of claim 1, wherein the imager is selected from the group consisting of a magnetic resonance imager, a positron emission tomograph and a computer tomograph.

11. The method of claim 1, wherein the T-type calcium channel inhibitor is administered to a concentration in a mammal's plasma of about 1 μM to about 10 μM.

12. The method of claim 1, wherein T-type calcium channel inhibitor is mibefradil.

13. The method of claim 1, wherein the disease is a cancer.

14. The method of claim 13, wherein the disease is a cancerous tumor.

15. The method of claim 13, wherein the T-type calcium channel inhibitor is mibefradil.

16. The method of claim 1, wherein the disease is pre-cancerous.

17. The method of claim 1, wherein the imaging marker is a positron emission tomography marker.

18. The method of claim 1, wherein the imaging marker is 2-deoxy-2-($^{18}$F)fluoro-D-glucose.

19. The method of claim 1, wherein the imager is a positron emission tomograph.

20. A method for increasing the sensitivity of imaging a cancer in a human which comprises the steps of:
(a) administering to the human an effective amount of mibefradil that inhibits proliferation of cancer cells by inhibiting cell cycle progression through the checkpoint between the G1 and S phase wherein the cancer cells accumulate at the G1/S checkpoint of the cell cycle;
(b) subsequently administering an imaging marker to the human after a period wherein cells that have accumulated at the G1/S checkpoint of the cell cycle following administration of the T-type calcium channel inhibitor have progressed to the S phase of the cell cycle, resulting in an increased proportion of the diseased cells in the S phase of the cell cycle; and
(c) imaging the human with an imager and obtaining an image of cancer cells with greater sensitivity compared with imaging in the absence of administration of the mibefradil.

21. The method according to claim 20, wherein the imaging marker is 2-deoxy-2-($^{18}$F)fluoro-D-glucose and the imager is a positron emission tomograph.

* * * * *